US012599687B2

(12) United States Patent
Ophardt et al.

(10) Patent No.: US 12,599,687 B2
(45) Date of Patent: Apr. 14, 2026

---

(54) FLUID DISPENSER WITH UV SANITATION

(71) Applicant: OP-Hygiene IP GmbH, Niederbipp (CH)

(72) Inventors: Heiner Ophardt, Arisdorf (CH);
Andrew Jones, St. Anns (CA);
Siegfried Steltenkamp, Bonn (DE);
Julie Claudinon, Freiburg (DE)

(73) Assignee: OP-HYGIENE IP GMBH, Niederbipp (CH)

( * ) Notice: Subject to any disclaimer, the term of this patent is extended or adjusted under 35 U.S.C. 154(b) by 391 days.

(21) Appl. No.: 18/323,817

(22) Filed: May 25, 2023

(65) Prior Publication Data

US 2023/0390440 A1     Dec. 7, 2023

Related U.S. Application Data

(60) Provisional application No. 63/347,778, filed on Jun. 1, 2022.

(51) Int. Cl.

| | |
|---|---|
| *A61L 2/10* | (2026.01) |
| *A47K 5/16* | (2006.01) |
| *A61L 2/088* | (2026.01) |
| *A61L 2/26* | (2006.01) |

(52) U.S. Cl.
CPC ...... *A61L 2/10* (2013.01); *A47K 5/16* (2013.01); *A61L 2/088* (2013.01); *A61L 2/26* (2013.01); *A61L 2202/11* (2013.01)

(58) Field of Classification Search
CPC ............... B67D 1/07; B67D 1/0861; B67D 2210/00015; A45D 27/02; A45D 27/04; A45D 27/06; A45D 27/10; A45D 27/12; A47K 5/1207; A47K 5/1217; A61L 2/10; A61L 2/16; A61L 2/26
USPC .......................................... 222/190
See application file for complete search history.

(56) References Cited

U.S. PATENT DOCUMENTS

| | | | | |
|---|---|---|---|---|
| 5,441,179 | A * | 8/1995 | Marsh ..................... | B67D 3/00 |
| | | | | 210/172.6 |
| 6,360,556 | B1* | 3/2002 | Gagliano ............. | B67D 1/0006 |
| | | | | 62/396 |
| 6,375,459 | B1* | 4/2002 | Kamen .............. | A61C 17/0208 |
| | | | | 604/35 |
| 6,443,335 | B1* | 9/2002 | Pinedjian ............. | B67D 1/0861 |
| | | | | 141/2 |
| 7,418,981 | B2 | 9/2008 | Baker et al. | |
| 8,359,877 | B2 | 1/2013 | Kamen et al. | |
| 8,672,187 | B2 | 3/2014 | Ophardt | |
| 9,936,841 | B2 | 4/2018 | Ophardt et al. | |
| 10,654,702 | B2* | 5/2020 | Kasprzycki .............. | B67D 1/14 |
| 2001/0010318 | A1* | 8/2001 | Saveliev .................. | B67D 1/07 |
| | | | | 422/186.3 |
| 2004/0232173 | A1* | 11/2004 | Saveliev ............. | B67D 1/1455 |
| | | | | 222/547 |

(Continued)

*Primary Examiner* — Charles P. Cheyney
(74) *Attorney, Agent, or Firm* — Thorpe North & Western, LLP

(57) ABSTRACT

A hand cleaning foam dispenser, including a reservoir providing a supply of foamable liquid; an air compartment providing a supply of air; a foam generator that mixes the foamable liquid and the air to produce a foam; a liquid pump for delivering the foamable liquid to the foam generator; an air pump for delivering the air to the foam generator; and a wave emitter that emits a wave into the air compartment to sanitize the air compartment.

12 Claims, 12 Drawing Sheets

(56)                    References Cited

U.S. PATENT DOCUMENTS

| | | | | |
|---|---|---|---|---|
| 2007/0175196 A1* | 8/2007 | Tepper | ............... | B01J 20/28054 |
| | | | | 55/527 |
| 2010/0288788 A1* | 11/2010 | Ophardt | ............... | A47K 5/1207 |
| | | | | 222/1 |
| 2013/0119083 A1* | 5/2013 | Ophardt | ............... | A47K 5/1211 |
| | | | | 222/64 |
| 2015/0056096 A1* | 2/2015 | Hoover | ................... | A61L 9/205 |
| | | | | 422/24 |
| 2015/0060493 A1* | 3/2015 | Duquet | .................... | A61L 2/10 |
| | | | | 222/148 |
| 2025/0176768 A1* | 6/2025 | Orban | ....................... | A61L 2/20 |

* cited by examiner

FLUID DISPENSER WITH UV SANITATION

RELATED APPLICATION

This application claims priority to the Jun. 1, 2022 filing date of U.S. Provisional Patent Application No. 63/347,778, which is incorporated herein by reference.

FIELD OF THE INVENTION

This invention relates to a hand cleaning foam dispenser, and more particularly to a foam dispenser that uses ultraviolet light to sanitize an internal compartment of the dispenser.

BACKGROUND OF THE INVENTION

Hand cleaning fluids, such as soap and hand sanitizer, are often mixed with air and dispensed in the form of a foam. Typically, the air that is used to make the foam is drawn into the dispenser from the external environment.

The inventors have appreciated a disadvantage of the prior art is that, when air is drawn into a dispenser to generate foam, there is a risk that the air is contaminated with an infectious agent, such as an airborne virus, bacteria and/or spores. For example, if an individual coughs or sneezes while using the dispenser, there is a risk that the air drawn into the dispenser could carry pathogens expelled by the cough or sneeze. The contaminated air would then be used to generate foam on a subsequent activation of the dispenser, potentially putting the next user of the dispenser at risk of becoming infected by the pathogen.

SUMMARY OF THE INVENTION

To at least partially overcome some of the disadvantages of previously known devices and methods, in one aspect the present invention provides a hand cleaning foam dispenser comprising: a reservoir providing a supply of foamable liquid; an air compartment providing a supply of air; a foam generator that mixes the foamable liquid and the air to produce a foam; a liquid pump for delivering the foamable liquid to the foam generator; an air pump for delivering the air to the foam generator; and a wave emitter that emits a wave into the air compartment to sanitize the air compartment. The wave may, for example, be in the form of electromagnetic radiation.

The inventors have appreciated that electromagnetic radiation, such as UVC, can advantageously be used to sterilize/sanitize the air compartment, and thereby reduce the risk of the dispenser transmitting infectious agents. Other types of waves, such as ultrasonic waves, could also be used to sanitize the air compartment.

The inventors have further appreciated that UVC suitable for sterilizing the air compartment can be generated using ultraviolet light-emitting diodes (LEDs) that require relatively low amounts of power. Use of electromagnetic radiation for sterilization also has a number of benefits in terms of costs, labor, safety, and/or environmental impacts compared to other possible methods of reducing contamination risks, such as autoclaving, single use pumps, and the use of sterilizing gases such as ethylene oxide or ozone.

Accordingly, in a first aspect the present invention resides in a hand cleaning foam dispenser comprising: a reservoir providing a supply of foamable liquid; an air compartment providing a supply of air; a foam generator that mixes the foamable liquid and the air to produce a foam; a liquid pump for delivering the foamable liquid to the foam generator; an air pump for delivering the air to the foam generator; and an electromagnetic radiation emitter that emits electromagnetic radiation into the air compartment to sanitize the air compartment.

In a second aspect, the present invention resides in a hand cleaning foam dispenser, which optionally incorporates one or more features of the first aspect, wherein the electromagnetic radiation emitter emits ultraviolet radiation.

In a third aspect, the present invention resides in a hand cleaning foam dispenser, which optionally incorporates one or more features of one or more of the first and second aspects, wherein the electromagnetic radiation emitter emits UVC.

In a fourth aspect, the present invention resides in a hand cleaning foam dispenser, which optionally incorporates one or more features of one or more of the first to third aspects, wherein the ultraviolet radiation has a wavelength of about 254 nm.

In a fifth aspect, the present invention resides in a hand cleaning foam dispenser, which optionally incorporates one or more features of one or more of the first to fourth aspects, wherein the electromagnetic radiation emitter comprises an ultraviolet light-emitting diode (LED).

In a sixth aspect, the present invention resides in a hand cleaning foam dispenser, which optionally incorporates one or more features of one or more of the first to fifth aspects, wherein the ultraviolet LED uses less than 5 J of energy per second.

In a seventh aspect, the present invention resides in a hand cleaning foam dispenser, which optionally incorporates one or more features of one or more of the first to sixth aspects, wherein the ultraviolet LED uses less than 4 J of energy per second.

In an eighth aspect, the present invention resides in a hand cleaning foam dispenser, which optionally incorporates one or more features of one or more of the first to seventh aspects, wherein the ultraviolet LED uses about 3.2 J of energy per second.

In a ninth aspect, the present invention resides in a hand cleaning foam dispenser, which optionally incorporates one or more features of one or more of the first to eighth aspects, wherein the air compartment comprises a compartment defining wall; wherein the electromagnetic radiation emitter is positioned outside of the air compartment; and wherein at least a portion of the compartment defining wall is formed from a material that permits the electromagnetic radiation to pass through the compartment defining wall into the air compartment.

In a tenth aspect, the present invention resides in a hand cleaning foam dispenser, which optionally incorporates one or more features of one or more of the first to ninth aspects, wherein the compartment defining wall is formed entirely from the material.

In an eleventh aspect, the present invention resides in a hand cleaning foam dispenser, which optionally incorporates one or more features of one or more of the first to tenth aspects, wherein the compartment defining wall has a window that is formed from the material.

In a twelfth aspect, the present invention resides in a hand cleaning foam dispenser, which optionally incorporates one or more features of one or more of the first to eleventh aspects, wherein the material comprises a cyclic olefin copolymer.

In a thirteenth aspect, the present invention resides in a hand cleaning foam dispenser, which optionally incorporates one or more features of one or more of the first to twelfth aspects, wherein the material comprises a polypropylene random copolymer.

In a fourteenth aspect, the present invention resides in a hand cleaning foam dispenser, which optionally incorporates one or more features of one or more of the first to thirteenth aspects, further comprising a housing and a foam pump, the foam pump comprising the air compartment, the liquid pump, the air pump, and the foam generator; wherein the housing is configured to removably receive the foam pump; and wherein the electromagnetic radiation emitter is arranged on the housing for emitting the electromagnetic radiation through the compartment defining wall into the air compartment when the foam pump is received by the housing.

In a fifteenth aspect, the present invention resides in a hand cleaning foam dispenser, which optionally incorporates one or more features of one or more of the first to fourteenth aspects, wherein the compartment defining wall is generally cylindrical, and the electromagnetic radiation emitter comprises a plurality of light-emitting diodes that are arranged radially around the compartment defining wall.

In a sixteenth aspect, the present invention resides in a hand cleaning foam dispenser, which optionally incorporates one or more features of one or more of the first to third aspects, wherein the air compartment comprises a surface that absorbs the electromagnetic radiation.

In a seventeenth aspect, the present invention resides in a hand cleaning foam dispenser, which optionally incorporates one or more features of one or more of the first to sixteenth aspects, wherein the surface comprises a UV activated material.

In an eighteenth aspect, the present invention resides in a hand cleaning foam dispenser, which optionally incorporates one or more features of one or more of the first to seventeenth aspects, wherein the UV activated material comprises titanium dioxide.

In a nineteenth aspect, the present invention resides in a hand cleaning foam dispenser, which optionally incorporates one or more features of one or more of the first to eighteenth aspects, wherein the UV activated material promotes photocatalytic production of reactive oxygen species when exposed to the electromagnetic radiation.

In a twentieth aspect, the present invention resides in a hand cleaning foam dispenser, which optionally incorporates one or more features of one or more of the first to nineteenth aspects, wherein the air compartment has an internal wall, and the surface comprises an outer surface of the internal wall.

In a twenty first aspect, the present invention resides in a hand cleaning foam dispenser, which optionally incorporates one or more features of one or more of the first to twentieth aspects, wherein the internal wall is cylindrical.

In a twenty second aspect, the present invention resides in a hand cleaning foam dispenser, which optionally incorporates one or more features of one or more of the first to twenty first aspects, further comprising a liquid compartment that receives the foamable liquid from the reservoir; wherein the outer surface surrounds the liquid compartment.

In a twenty third aspect, the present invention resides in a hand cleaning foam dispenser, which optionally incorporates one or more features of one or more of the first to twenty second aspects, wherein the electromagnetic radiation emitter is configured to only emit the electromagnetic radiation when the foam pump is received by the housing.

In a twenty fourth aspect, the present invention resides in a hand cleaning foam dispenser, which optionally incorporates one or more features of one or more of the first to twenty third aspects, further comprising a switch that is activated when the foam pump is received by the housing; and wherein the electromagnetic radiation emitter is configured to only emit the electromagnetic radiation when the switch is activated.

In a twenty fifth aspect, the present invention resides in a hand cleaning foam dispenser, which optionally incorporates one or more features of one or more of the first to twenty fourth aspects, wherein the housing has a lock-out mechanism to prevent unauthorized pumps from being received by the housing; wherein the foam pump has a lock-out structure that engages with the lock-out mechanism when the foam pump is received by the housing; and wherein the switch is located on or adjacent to the lock-out mechanism, so that the lock-out structure activates the switch when the foam pump is received by the housing.

In a twenty sixth aspect, the present invention resides in a hand cleaning foam dispenser, which optionally incorporates one or more features of one or more of the first to twenty fifth aspects, wherein the air compartment comprises a compartment defining wall; wherein the compartment defining wall has an emitter receiving opening; and wherein the electromagnetic radiation emitter extends through the emitter receiving opening for emitting the electromagnetic radiation into the air compartment.

In a twenty seventh aspect, the present invention resides in a hand cleaning foam dispenser, which optionally incorporates one or more features of one or more of the first to twenty sixth aspects, wherein the emitter receiving opening engages with the electromagnetic radiation emitter to form a fluid tight seal there between.

In a twenty eighth aspect, the present invention resides in a hand cleaning foam dispenser, which optionally incorporates one or more features of one or more of the first to twenty seventh aspects, further comprising a housing and a foam pump, the foam pump comprising the air compartment, the liquid pump, the air pump, and the foam generator; wherein the housing is configured to removably receive the foam pump; and wherein the electromagnetic radiation emitter is arranged on the housing to be received by the emitter receiving opening when the foam pump is received by the housing.

In a twenty ninth aspect, the present invention resides in a hand cleaning foam dispenser, which optionally incorporates one or more features of one or more of the first to twenty eighth aspects, wherein the air pump is inoperable to deliver the air to the foam generator when the electromagnetic radiation emitter is absent from the emitter receiving opening.

In a thirtieth aspect, the present invention resides in a hand cleaning foam dispenser, which optionally incorporates one or more features of one or more of the first to twenty ninth aspects, wherein the electromagnetic radiation emitter is positioned inside the air compartment.

In a thirty first aspect, the present invention resides in a hand cleaning foam dispenser, which optionally incorporates one or more features of one or more of the first to thirtieth aspects, wherein the air compartment has a generally cylindrical shape, with a first axial end and a second axial end; and wherein the electromagnetic radiation emitter is positioned at the first axial end of the air compartment.

In a thirty second aspect, the present invention resides in a hand cleaning foam dispenser, which optionally incorporates one or more features of one or more of the first to thirty first aspects, wherein the electromagnetic radiation emitter comprises a plurality of light-emitting diodes that are arranged radially around a central axis of the air compartment.

In a thirty third aspect, the present invention resides in a hand cleaning foam dispenser, which optionally incorporates one or more features of one or more of the first to thirty second aspects, further comprising a housing and a foam pump, the foam pump comprising the air compartment, the liquid pump, the air pump, the foam generator, and the electromagnetic radiation emitter; wherein the housing is configured to removably receive the foam pump.

In a thirty fourth aspect, the present invention resides in a foam pump, which optionally incorporates one or more features of one or more of the first to thirty third aspects, comprising: a foam generator that mixes foamable liquid and air to produce a foam; a liquid pump for delivering the foamable liquid to the foam generator; an air compartment providing a supply of air; an air pump for delivering the air to the foam generator; and an electromagnetic radiation emitter that emits electromagnetic radiation into the air compartment to sanitize the air compartment.

In a thirty fifth aspect, the present invention resides in a foam pump, which optionally incorporates one or more features of one or more of the first to thirty fourth aspects, comprising: a foam generator that mixes foamable liquid and air to produce a foam; a liquid pump for delivering the foamable liquid to the foam generator; an air compartment providing a supply of air; and an air pump for delivering the air to the foam generator; wherein the air compartment comprises a compartment defining wall; and wherein at least a portion of the compartment defining wall is formed from a material that permits electromagnetic radiation to pass through the compartment defining wall into the air compartment.

In a thirty sixth aspect, the present invention resides in a foam pump, which optionally incorporates one or more features of one or more of the first to thirty fifth aspects, comprising: a foam generator that mixes foamable liquid and air to produce a foam; a liquid pump for delivering the foamable liquid to the foam generator; an air compartment providing a supply of air; and an air pump for delivering the air to the foam generator; wherein the air compartment comprises a compartment defining wall; and wherein the compartment defining wall has an emitter receiving opening for receiving an electromagnetic radiation emitter.

In a thirty seventh aspect, the present invention resides in a foam pump, which optionally incorporates one or more features of one or more of the first to thirty sixth aspects, wherein the foam pump comprises the foam pump as defined in any one of the first to thirty third aspects.

In a thirty eighth aspect, the present invention resides in a method, which optionally incorporates one or more features of one or more of the first to thirty seventh aspects, comprising: providing the hand cleaning foam dispenser as defined in any one of the first to thirty third aspects; and emitting the electromagnetic radiation from the electromagnetic radiation emitter into the air compartment to sanitize the air compartment.

In a thirty ninth aspect, the present invention resides in a method, which optionally incorporates one or more features of one or more of the first to thirty eighth aspects, further comprising: placing the foam pump into the housing.

In a fortieth aspect, the present invention resides in a method, which optionally incorporates one or more features of one or more of the first to thirty ninth aspects, further comprising: dispensing the foam from the hand cleaning foam dispenser.

In a forty first aspect, the present invention resides in a hand cleaning foam dispenser, which optionally incorporates one or more features of one or more of the first to fortieth aspects, comprising: a reservoir providing a supply of foamable liquid; an air compartment providing a supply of air; a foam generator that mixes the foamable liquid and the air to produce a foam; a liquid pump for delivering the foamable liquid to the foam generator; an air pump for delivering the air to the foam generator; and a wave emitter that emits a wave into the air compartment to sanitize the air compartment.

In a forty second aspect, the present invention resides in a hand cleaning foam dispenser, which optionally incorporates one or more features of one or more of the first to forty first aspects, wherein the wave emitter comprises an electromagnetic radiation emitter that emits electromagnetic radiation into the air compartment to sanitize the air compartment.

In a forty third aspect, the present invention resides in a hand cleaning foam dispenser, which optionally incorporates one or more features of one or more of the first to forty second aspects, wherein the surface comprises a material that has an antibacterial effect that is activated or enhanced when the surface is exposed to the electromagnetic radiation.

In a forty fourth aspect, the present invention resides in a foam pump, which optionally incorporates one or more features of one or more of the first to forty third aspects, comprising: a foam generator that mixes foamable liquid and air to produce a foam; a liquid pump for delivering the foamable liquid to the foam generator; an air compartment providing a supply of air; an air pump for delivering the air to the foam generator; and a wave emitter that emits a wave into the air compartment to sanitize the air compartment.

In a forty fifth aspect, the present invention resides in a foam pump, which optionally incorporates one or more features of one or more of the first to forty fourth aspects, comprising: a foam generator that mixes foamable liquid and air to produce a foam; a liquid pump for delivering the foamable liquid to the foam generator; an air compartment providing a supply of air; and an air pump for delivering the air to the foam generator; wherein the air compartment comprises a compartment defining wall; and wherein the compartment defining wall has an emitter receiving opening for receiving a wave emitter.

In a forty sixth aspect, the present invention resides in a method, which optionally incorporates one or more features of one or more of the first to forty fifth aspects, comprising: providing the hand cleaning foam dispenser in accordance with any one or more of the preceding aspects; and emitting the wave from the wave emitter into the air compartment to sanitize the air compartment.

BRIEF DESCRIPTION OF THE DRAWINGS

Further aspects and advantages of the invention will appear from the following description taken together with the accompanying drawings, in which.

DETAILED DESCRIPTION OF THE DRAWINGS

Figure 1:
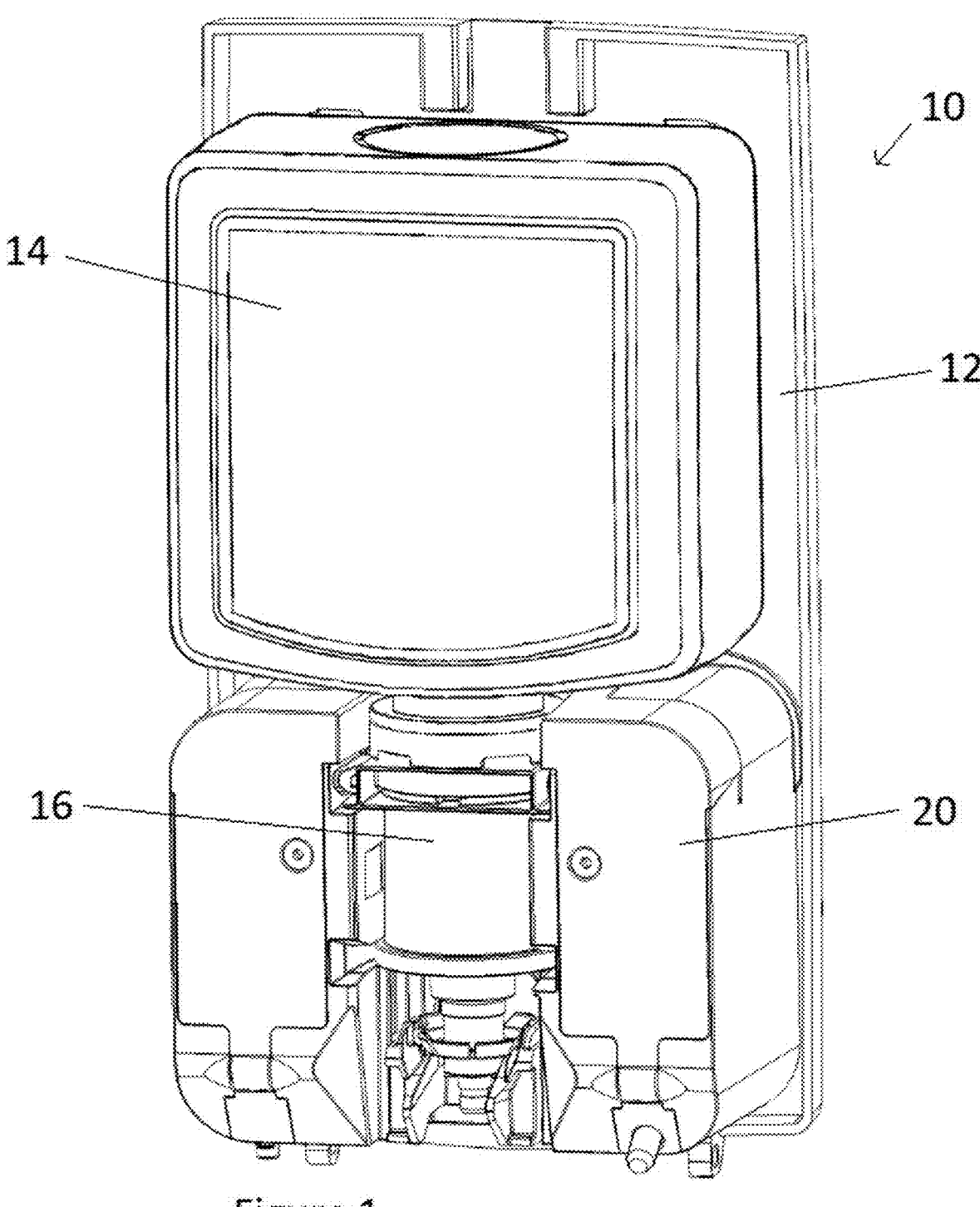
FIG. 1 is a perspective view of a foam dispenser in accordance with a first embodiment of the present invention.

FIG. 1 shows a foam dispenser 10 in accordance with a first embodiment of the present invention. The dispenser 10 has a housing 12, a reservoir 14, and a piston pump 16. The foam dispenser 10 is operable to dispense foam from the piston pump 16 on activation of the pump 16, as is known in the art. The foam dispenser 10 can optionally be touchlessly activated, as by a sensor detecting a user's hand placed below the piston pump 16. Alternatively, the dispenser 10 could be configured to be manually activated.

Figure 2:
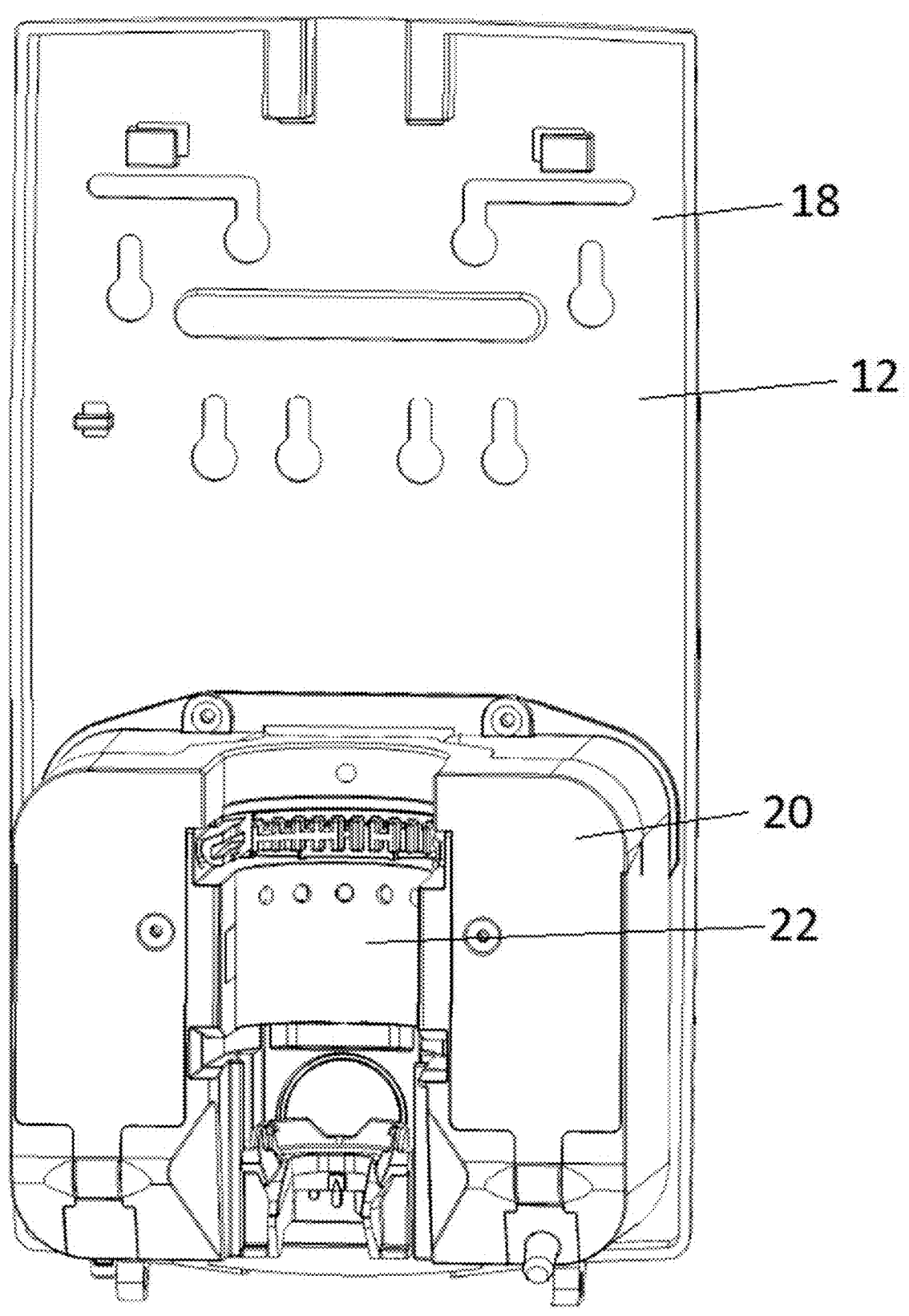
FIG. 2 is a perspective view of a housing of the foam dispenser shown in FIG. 1.

The housing 12 is best shown in FIG. 2 as including a back plate 18 and a pump mounting body 20. The housing 12 also optionally includes a removable cover, not shown, that attaches to the back plate 18 to cover the reservoir 14, the piston pump 16, and the pump mounting body 20.

The back plate 18 is configured to be secured to a vertical support surface, such as a wall or a post. The pump mounting body 20 extends forwardly from a bottom portion of the back plate 18. The pump mounting body 20 has a central pump engagement cavity 22 for removably receiving the piston pump 16. The pump mounting body 20 includes a catch mechanism 24 for engaging with a piston forming element 28 of the piston pump 16, and a pump holding mechanism 26 for engaging with a piston chamber forming body 30 of the piston pump 16. As is known in the art, the catch mechanism 24 is configured to move vertically relative to the pump holding mechanism 26 on activation of the dispenser 10, to move the piston forming element 28 of the piston pump 16 vertically relative to the piston chamber forming body 30 of the piston pump 16, to thereby dispense foam from the piston pump 16.

Figure 3:
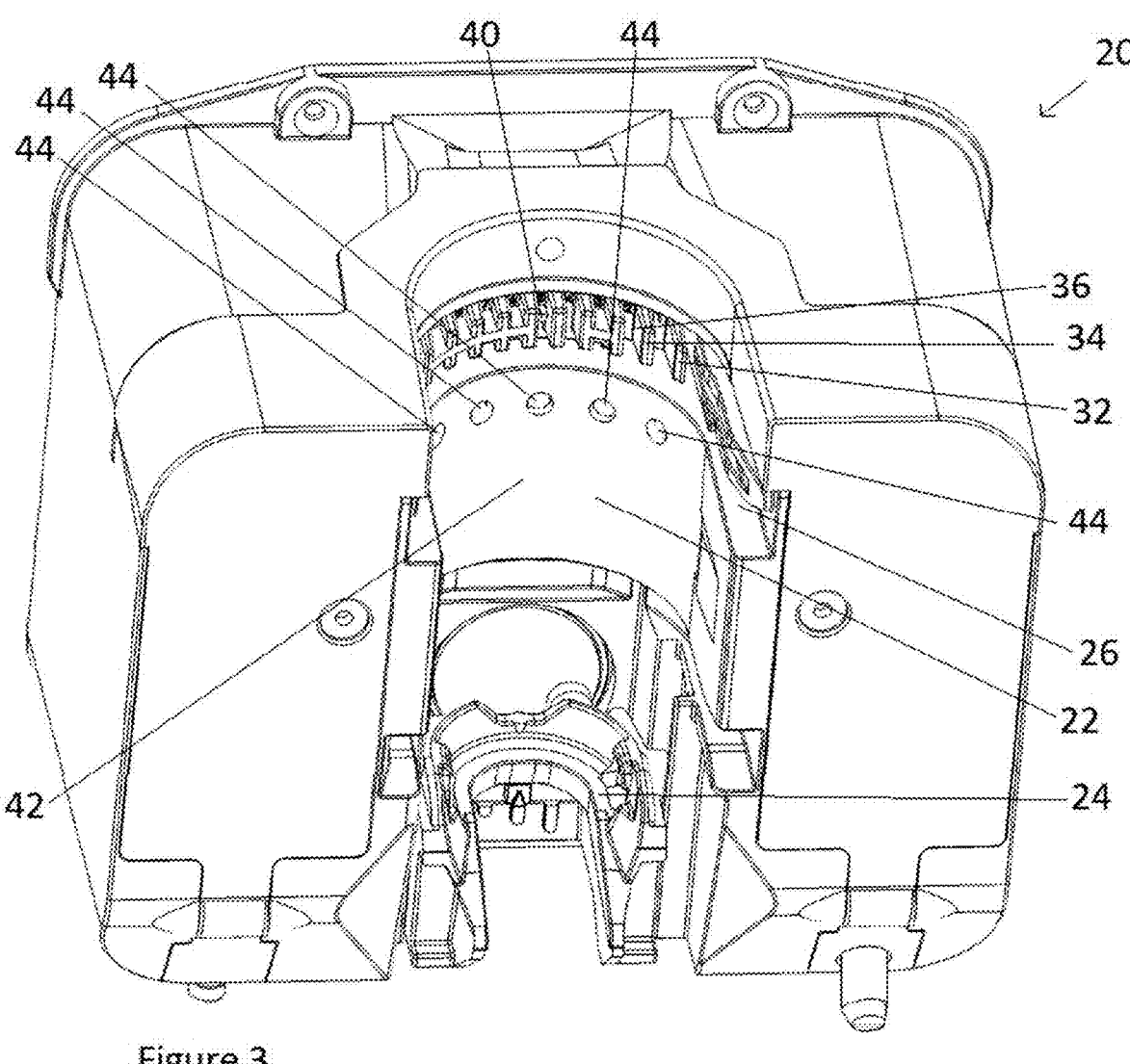
FIG. 3 is a perspective view of a pump mounting body of the housing shown in FIG. 2.

As can be seen in FIG. 3, the pump holding mechanism 26 includes a lock-out mechanism 32 formed by a series of projections 34 that extend forwardly in a pre-selected unique arrangement, with notches 36 defined between the projections 34. The lock-out mechanism 32 is configured to engage with a lock-out structure 38 on the piston pump 16 when the piston pump 16 is received by the pump holding mechanism 26.

As can be seen in FIG. 3, a trigger member 40 is positioned in one of the notches 36 of the lock-out mechanism 32. The trigger member 40 is configured to be depressed by the lock-out structure 38 of the piston pump 16 when the piston pump 16 is received by the pump holding mechanism 26.

Referring again to FIG. 3, the pump engagement cavity 22 has a concave surface 42 that extends downwardly below the pump holding mechanism 26. A series of ultraviolet light emitting diodes 44 are positioned in a horizontal arc near the top of the concave surface 42. The ultraviolet light emitting diodes 44 are configured to emit ultraviolet light when activated, preferably UVC with a wavelength of about 254 nm.

The reservoir 14, which is shown in FIG. 1, is a bottle that contains a supply of a hand cleaning fluid, such as soap or hand sanitizer. The reservoir 14 connects to the piston pump 16 for delivering the fluid to the piston pump 16, as is known in the art.

Figure 4:
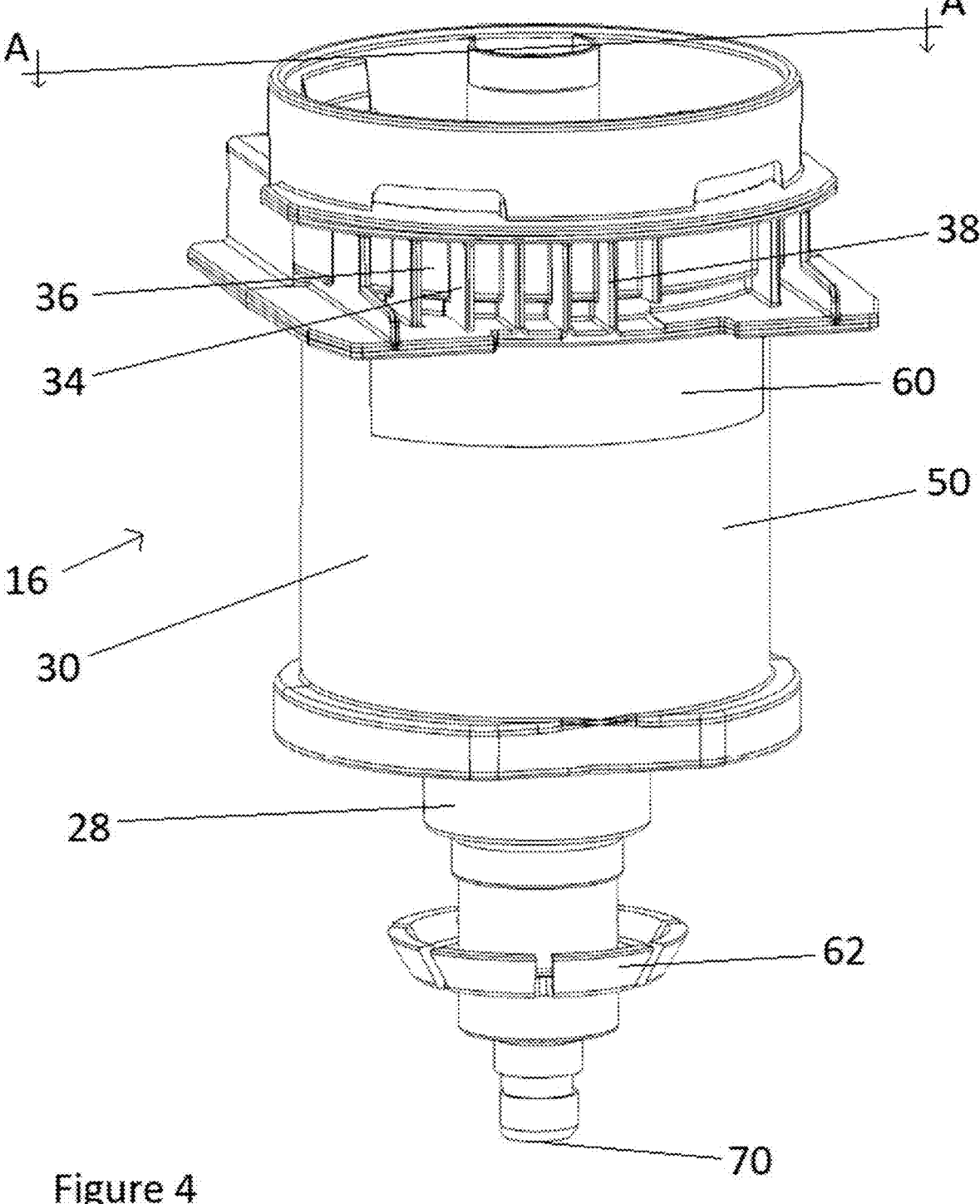
FIG. 4 is a perspective view of a foam pump of the foam dispenser shown in FIG. 1.
Figure 5:
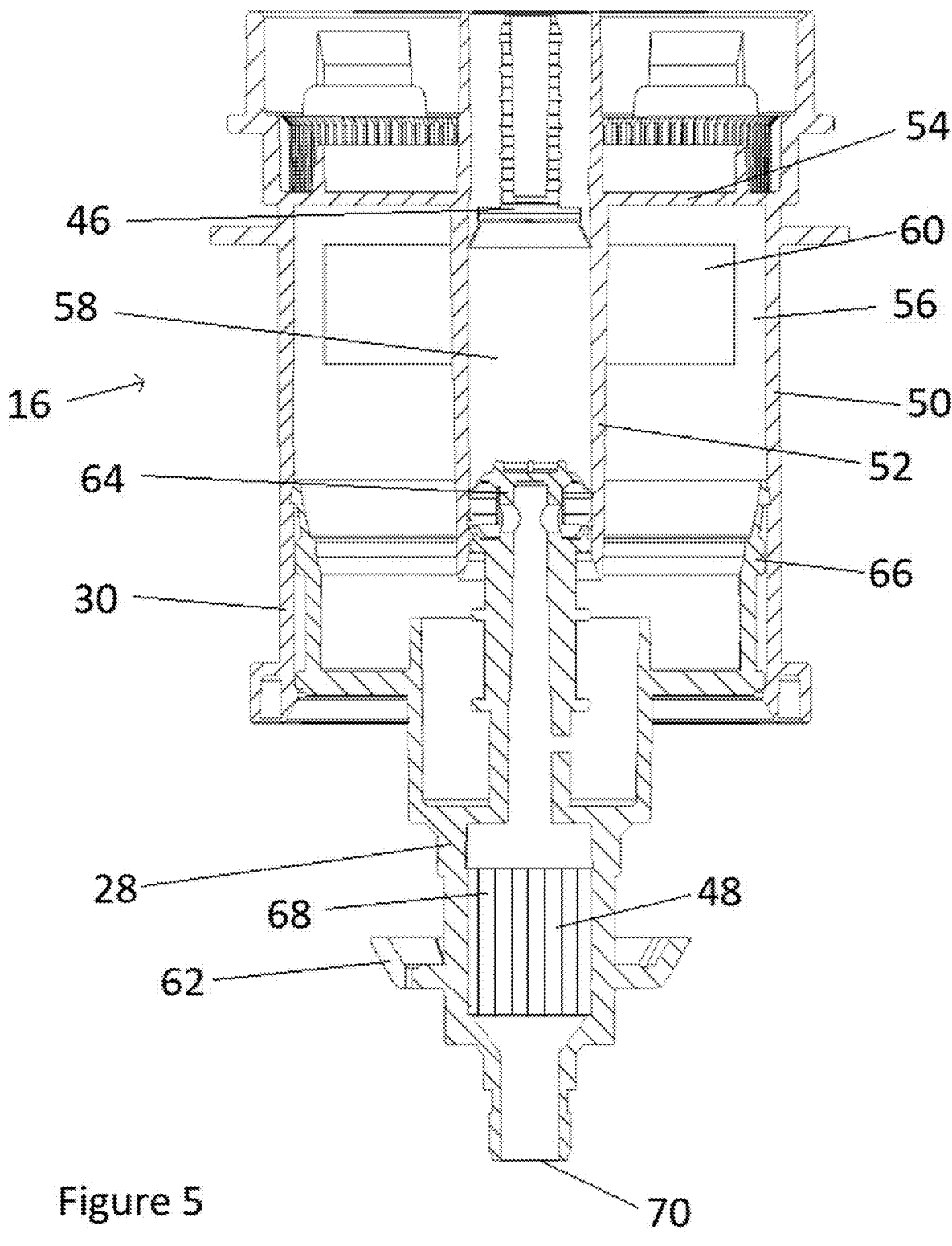
FIG. 5 is cross-sectional view of the foam pump shown in FIG. 4, taken along line A-A' shown in FIG. 4.

As can be seen in FIGS. 4 and 5, the piston pump 16 has a piston forming element 28, a piston chamber forming body 30, a one-way fluid inlet valve 46, and a foam generator 48.

Referring to FIG. 4, the piston chamber forming body 30 has a lock-out structure 38 formed by a series of projections 34 with notches 36 therebetween. The projections 34 and notches 36 of the lock-out structure 38 are arranged to be complimentary to the projections 34 and notches 36 of the lock-out mechanism 32, such that the projections 34 of the lock-out structure 38 are received by the notches 36 of the lock-out mechanism 32 and the projections 34 of the lock-out mechanism 32 are received by the notches 36 of the lock-out structure 38 when the piston pump 16 is received by the pump mounting body 20.

Referring to FIG. 5, the piston chamber forming body 30 has an outer cylindrical wall 50, an inner cylindrical wall 52, and an upper terminal wall 54. An air chamber 56 with an open bottom end is defined between the outer cylindrical wall 50, the inner cylindrical wall 52, and the upper terminal wall 54. A liquid chamber 58 with an open bottom end is defined by the inner cylindrical wall 52 and the one-way fluid inlet valve 46.

As can be seen in FIG. 4, the outer cylindrical wall 50 has a window 60 that is formed from a material that permits the ultraviolet light emitted by the light emitting diodes 44 to pass through the window 60. The window 60 may, for example, be formed from a cyclic olefin copolymer such as TOPAS™ 80075-04 COC or a polypropylene random copolymer such as BRASKEM™ RP350.

As can be seen in FIG. 4, the piston forming element 28 has a catch member 62 that is configured to engage with the catch mechanism 24 of the pump mounting body 20, as is known in the art. As can be seen in FIG. 5, the piston forming element 28 has a liquid piston element 64 and an air piston element 66. The liquid piston element 64 is received in the open bottom end of the liquid chamber 58, and the air piston element 66 is received in the open bottom end of the air chamber 56.

The piston forming element 28 also defines a foam generating chamber 68 that carries the foam generator 48. The foam generator 48 optionally includes a porous sponge member sandwiched between two screens, though any suitable structure for generating foam could be used.

As is known in the art, the piston pump 16 is configured to generate foam on vertical movement of the piston forming element 28 relative to the piston chamber forming body 30. When in an extended position as shown in FIG. 5, the air chamber 56 is filled with air and the liquid chamber 58 is filled with hand cleaning liquid. On movement of the piston forming element 28 upwardly relative to the piston chamber forming body 30, the air in the air chamber 56 is compressed by the air piston element 66, which forces the air into the foam generating chamber 68 and through the foam generator 48. Simultaneously, the liquid in the liquid chamber 58 is compressed by the liquid piston element 64, which forces the liquid into the foam generating chamber 68 and through the foam generator 48. The foam generator 48 causes the air and the liquid passing therethrough to turbulently mix, forming a foam, which is expelled from a discharge outlet 70 of the piston pump 16.

On movement of the piston forming element 28 downwardly back to the extended position shown in FIG. 5, the downwards movement of the air piston element 66 generates a vacuum within the air chamber 56, drawing air into the air chamber 56 via the discharge outlet 70. The downwards movement of the liquid piston element 64 likewise generates a vacuum within the liquid chamber 58, drawing liquid from the reservoir 14 past the one-way liquid inlet valve 46 and into the liquid chamber 58. With the air chamber 56 filled with air and the liquid chamber 58 filled with liquid, the piston pump 16 is ready to be activated again to dispense another allotment of foam.

The inventors have appreciated that the air drawn into the air chamber 56 may possibly contain contaminants, such as viruses or bacteria. To reduce the risk of the foam dispenser 10 spreading infectious agents via the discharged foam, the foam dispenser 10 is configured to periodically sterilize the air chamber 56 with ultraviolet radiation.

In particular, the ultraviolet LEDs 44 are configured to periodically emit ultraviolet radiation through the window 60 and into the air chamber 56 to thereby sterilize the air chamber 56. The inventors have appreciated that by arranging the ultraviolet LEDs 44 radially around the outer cylindrical wall 50, the ultraviolet light can be emitted through the window 60 at multiple different angles, to thereby flood the air chamber 56 with ultraviolet light and preferably provide extensive sterilization of the air chamber 56.

The ultraviolet LEDs 44 may be controlled in any suitable manner to provide the desired sterilization. For example, the LEDs 44 may be configured to emit ultraviolet radiation into the air chamber 56 immediately after each activation of the dispenser 10; while the air chamber 56 is being refilled with air; when the air chamber 56 is filled with air; immediately before each activation of the dispenser 10; and/or while the air is being expelled from the air chamber 56.

The duration and intensity of the ultraviolet radiation may be selected to provide the desired sterilization. For example, the ultraviolet radiation may be emitted for less than 5 seconds; less than 15 seconds; less than 30 seconds; less than 45 seconds; less than 1 minute; about 1 minute; or between 1 minute and 2 minutes. The LEDs 44 are preferably configured to have a relatively low level of power consumption, to reduce the energy consumption of the dispenser 10. Preferably, the LEDs 44 use less than 5 J of energy per second; less than 4 J of energy per second; or about 3.2 J of energy per second.

Optionally, to improve the sterilization of the air chamber 56, one or more surfaces of the air chamber 56 may include or be coated with a UV activated material, such as titanium dioxide. The UV activated material preferably promotes the photocatalytic production of reactive oxygen species when exposed to the UV radiation, to thereby enhance sterilization of the air chamber 56. The UV activated material may, for example, be present on the inner surface of the outer cylindrical wall 50, or on the outer surface of the inner cylindrical wall 52. Optionally, the UV activated material could be incorporated into a cylindrical sleeve, not shown, that surrounds the inner cylindrical wall 52.

In some embodiments of the invention, providing UV activated material in or around the inner cylindrical wall 52 is especially preferred, as the inner cylindrical wall 52 acts as a focal point for the UV radiation emitted from the radially arranged LEDs 44. Optionally, the material could be configured to be activated by other types of electromagnetic radiation, such as visible light. Preferably, the material produces an antibacterial effect when exposed to at least some wavelengths of electromagnetic radiation.

The LEDs 44 are preferably configured to only emit UV radiation when the piston pump 16 is received by the pump mounting body 20. In particular, the LEDs 44 are preferably configured to only emit UV radiation when the trigger member 40 is depressed. When the piston pump 16 is received by the pump mounting body 20, the lock-out structure 38 of the piston pump 16 engages with the lock-out mechanism 32 of the pump mounting body 20, and a projection 34 of the lock-out structure 38 depresses the trigger member 40. When the piston pump 16 is removed from the pump mounting body 20, the trigger member 40 is released and returns to an inactivated state, preventing the LEDs 44 from being activated. The LEDs 44 may, for example, be controlled by a controller, not shown, that detects when the trigger member is depressed.

Optionally, the pump mounting body 20 is also able to receive pumps, not shown, that are not configured for UV sterilization. These pumps preferably have a lock-out member that is able to engage with the lock-out mechanism 32 of the pump mounting body 20, but does not depress the trigger member 40. This ensures that the LEDs 44 do not emit UV radiation when a pump that is not suitable for UV sterilization is mounted to the pump mounting body 20.

Although the embodiment shown in FIGS. 1 to 5 includes a window 60 that is formed from a material that permits the ultraviolet light emitted by the light emitting diodes 44 to pass therethrough, it is to be appreciated that the entire outer cylindrical wall 50 could be made from the material.

Figure 6:
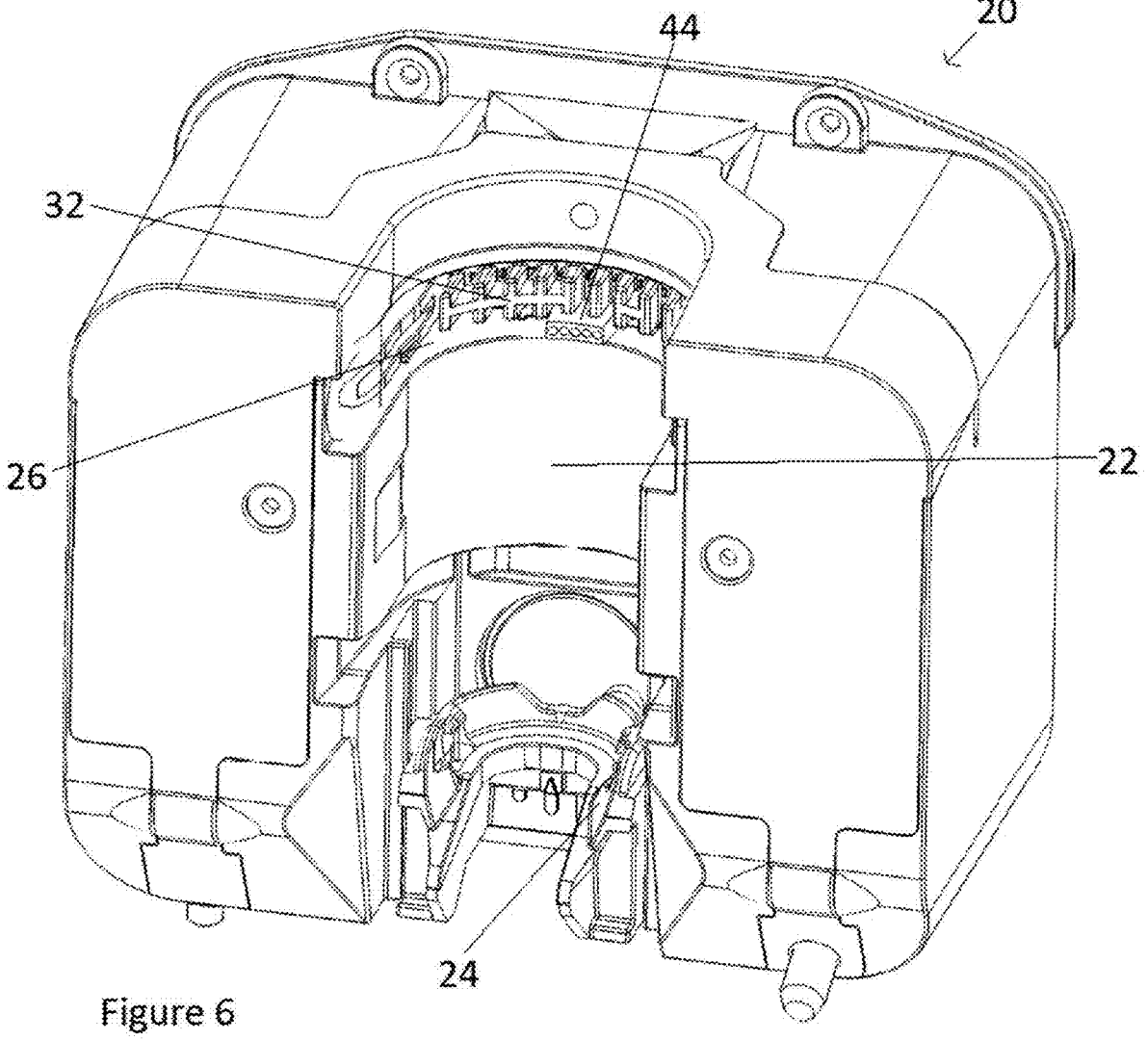
FIG. 6 is a perspective view of a pump mounting body of a foam dispenser in accordance with a second embodiment of the present invention.
Figure 7:
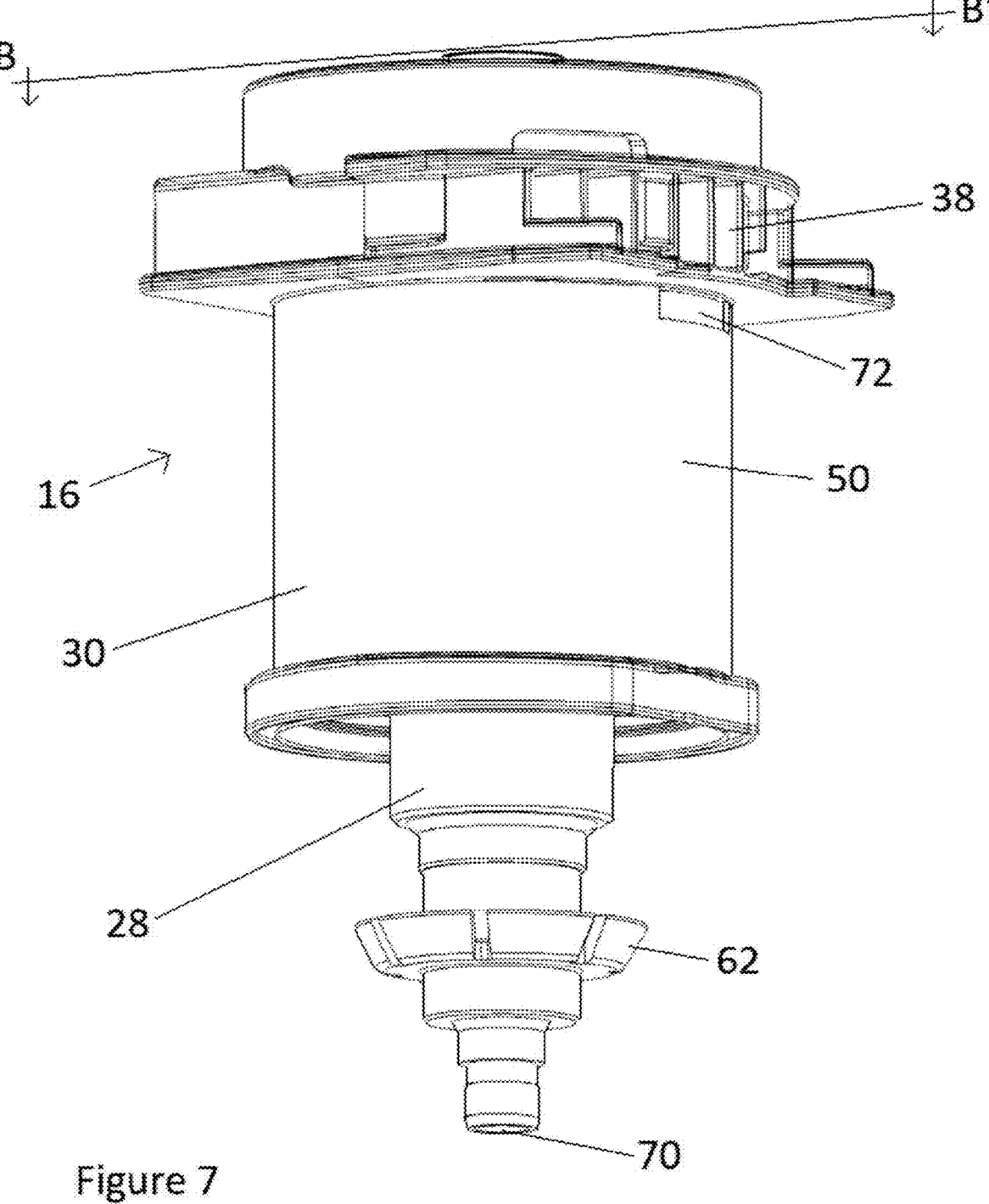
FIG. 7 is a perspective view of a foam pump of the foam dispenser in accordance with the second embodiment.
Figure 8:
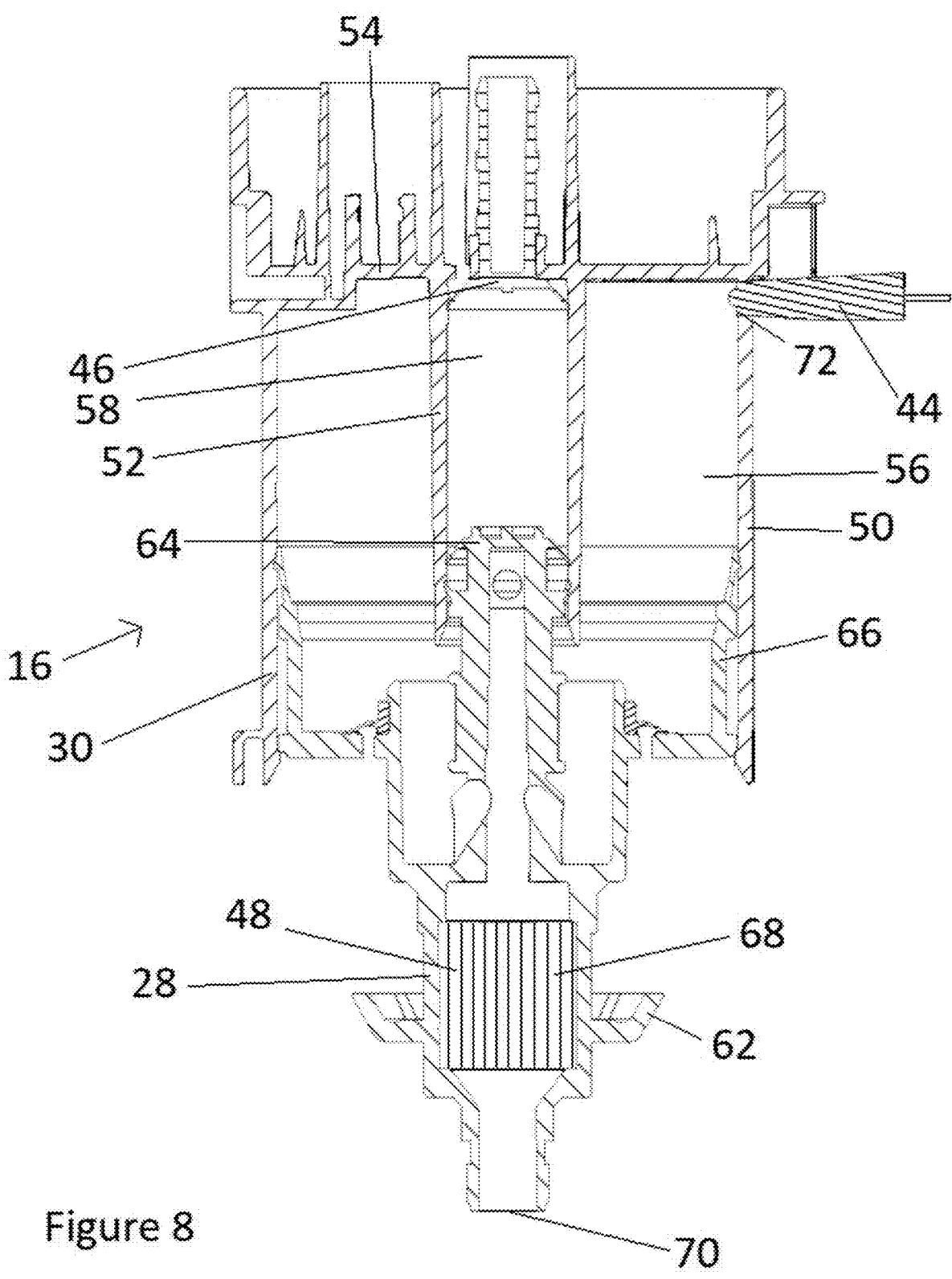
FIG. 8 is a cross-sectional view of the foam pump shown in FIG. 7, engaged with an electromagnetic emitter of the pump mounting body shown in FIG. 6, taken along line B-B' shown in FIG. 7.

Reference is now made to FIGS. 6 to 8, which show a fluid dispenser 10 in accordance with a second embodiment of the present invention. Like numerals are used to denote like components.

The fluid dispenser 10 shown in FIGS. 6 to 8 is identical to the fluid dispenser 10 shown in FIGS. 1 to 5, with the notable exception that the pump mounting body 20 has an LED 44 that is configured to extend into the air chamber 56, rather than being positioned outside the air chamber 56 as in FIGS. 1 to 5.

As can be seen in FIG. 6, the LED 44 extends forwardly from a rear surface of the pump engagement cavity 22, just below the lock-out mechanism 32. The outer cylindrical wall 50 of the piston chamber forming body 30 also has an emitter receiving opening 72 positioned just below the lock-out structure 38, as can be seen in FIG. 7. As can be seen in FIG. 8, the LED 44 extends into the air chamber 56 through the emitter receiving opening 72 when the piston pump 16 is received by the pump mounting body 20.

As in the previous embodiment, the LED 44 is configured to emit UV radiation into the air chamber 56 to sterilize the air chamber 56. The inventors have appreciated that by arranging the LED 44 to be inserted directly into the air chamber 56, the outer cylindrical wall 50 can be made without requiring the window 60. Furthermore, in the embodiment shown in FIGS. 6 to 8, there is no loss of UV radiation that might otherwise occur when the UV radiation passes through the window 60.

Preferably, the LED 44 forms a fluid tight seal when inserted into the emitter receiving opening 72, to thereby prevent air from being expelled or drawn in through the emitter receiving opening 72. The emitter receiving opening 72 also provides a lock-out function, by preventing the piston pump 16 from being used with a housing 12 that lacks the LED 44, since the emitter receiving opening 72 will prevent the pump 16 from generating foam unless the emitter receiving opening 72 is plugged. Similarly, the LED 44 will interfere with and prevent the housing 12 from receiving a pump that lacks an emitter receiving opening 72.

Figure 9:
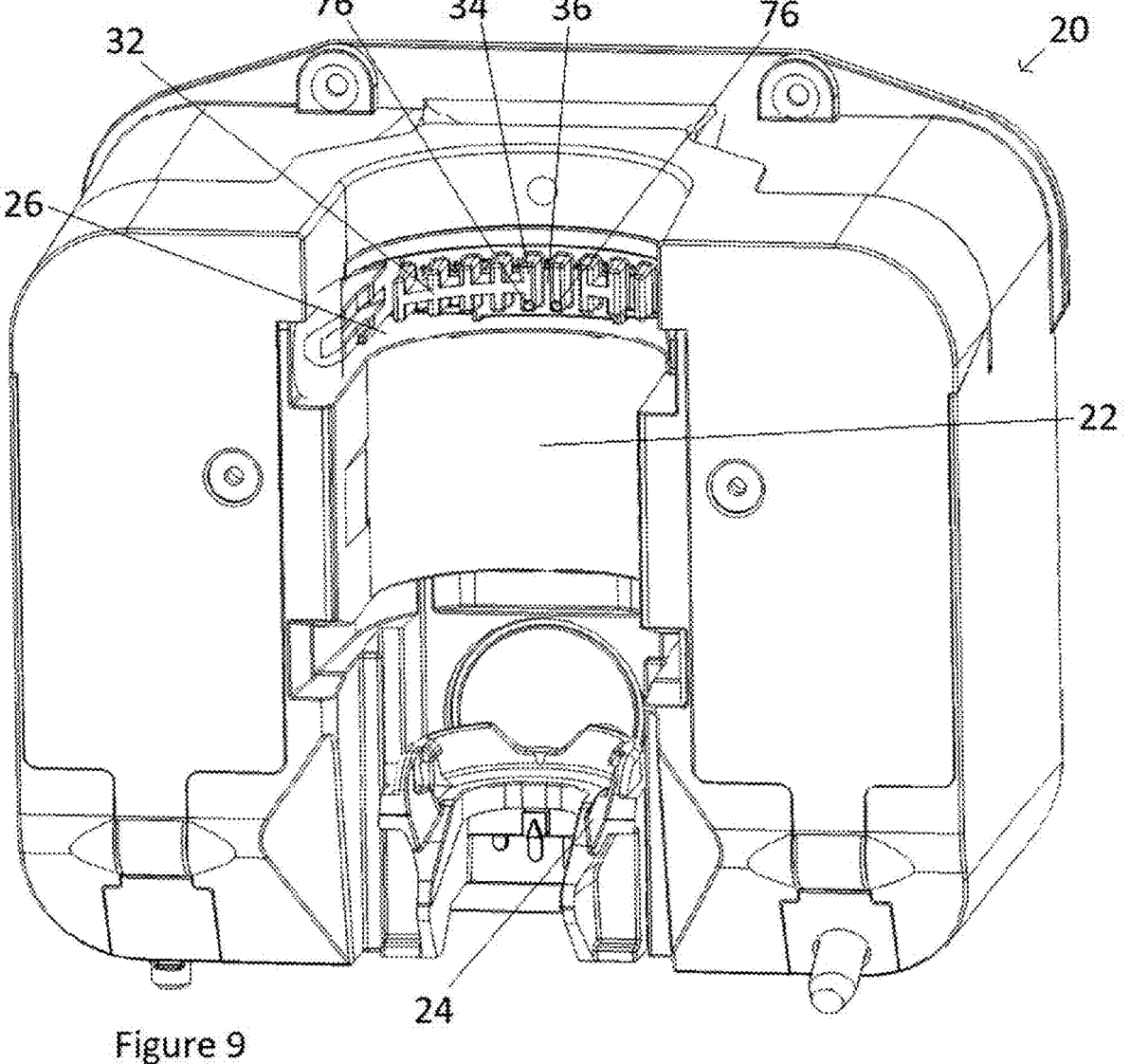
FIG. 9 is a perspective view of a pump mounting body of a foam dispenser in accordance with a third embodiment of the present invention.
Figure 10:
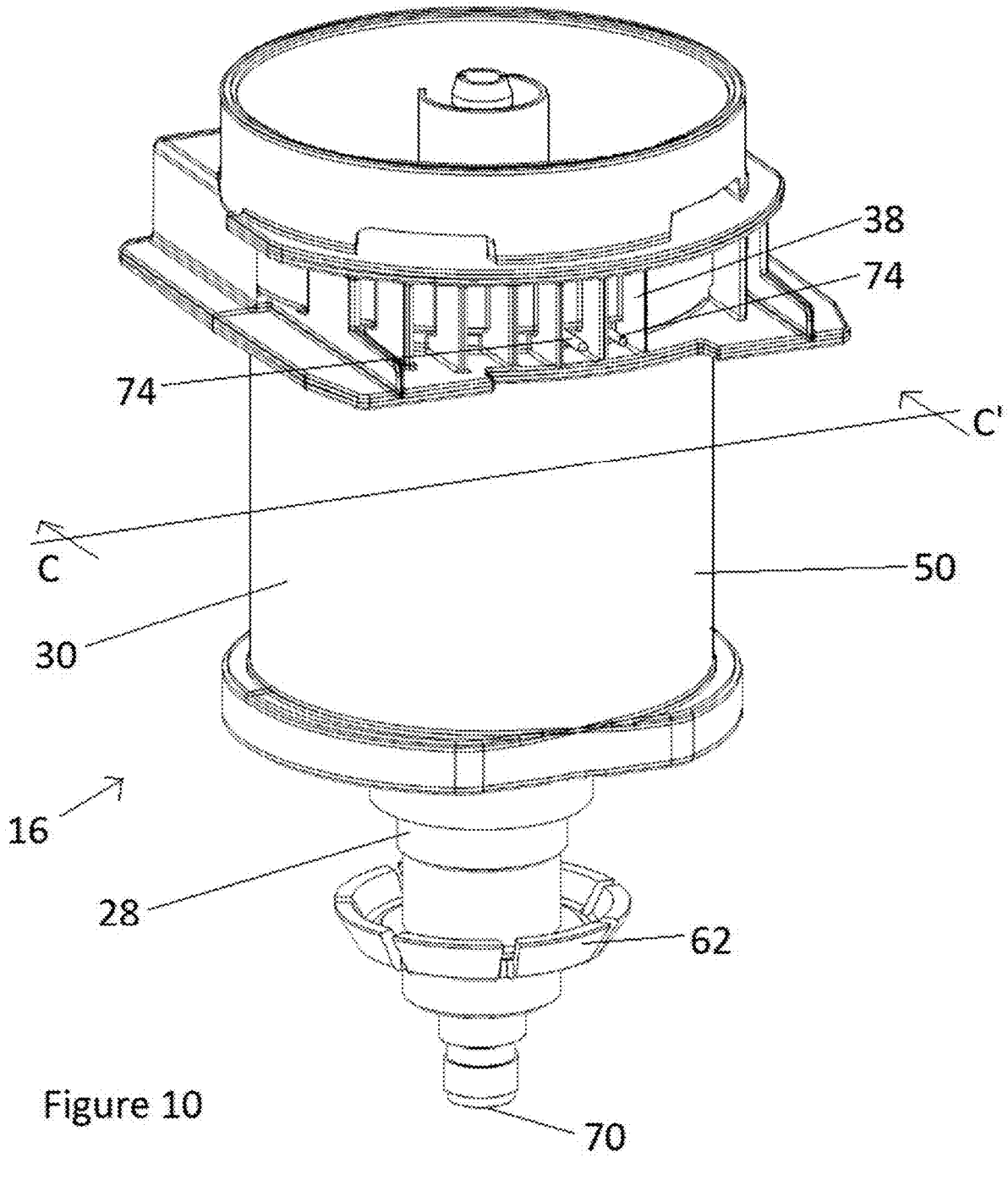
FIG. 10 is a perspective view of a foam pump of the foam dispenser in accordance with the third embodiment.
Figure 11:
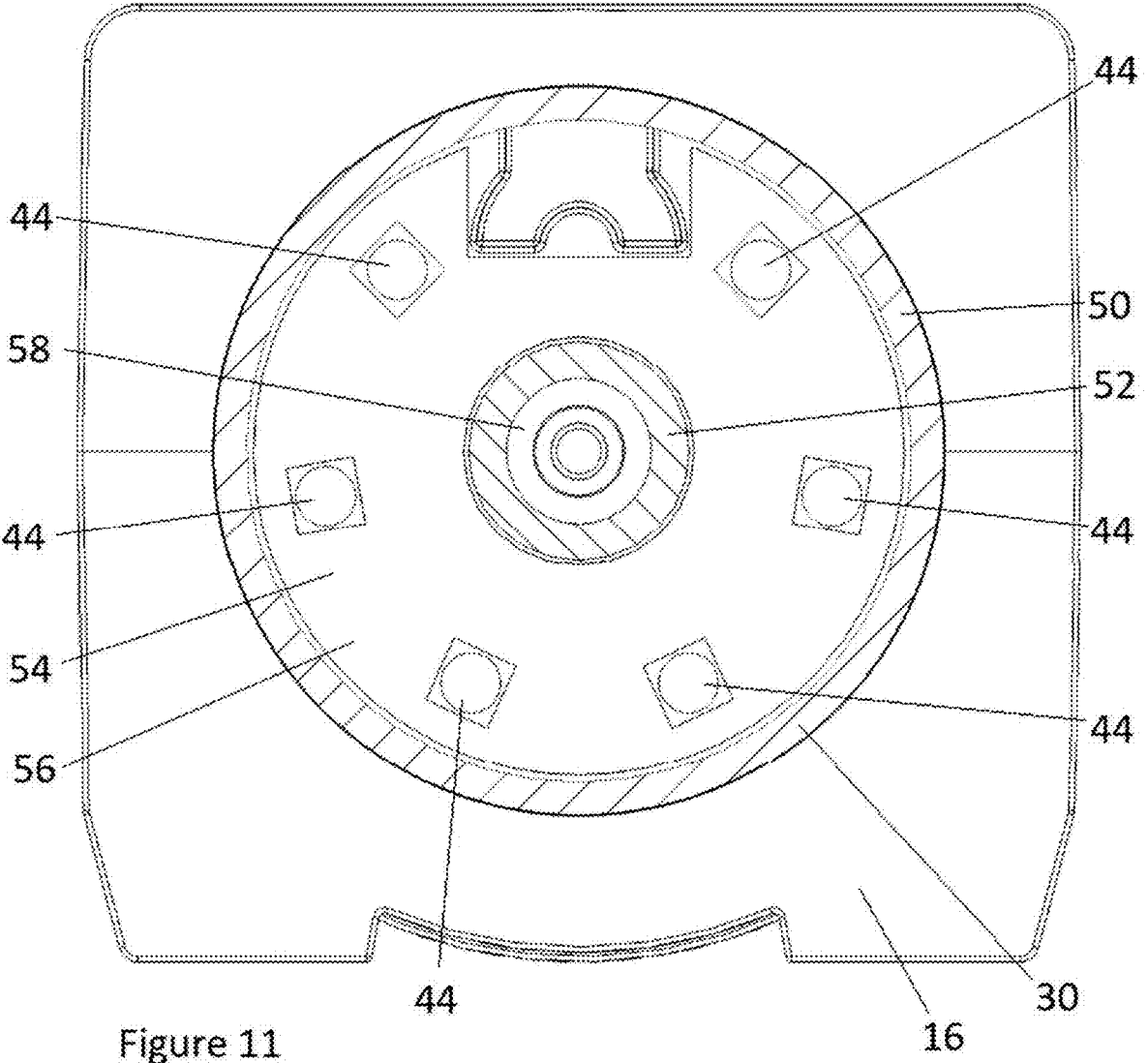
FIG. 11 is a cross-sectional view of the foam pump shown in FIG. 10, taken along line C-C' shown in FIG. 10.

Reference is now made to FIGS. 9 to 11, which show a fluid dispenser 10 in accordance with a third embodiment of the present invention. Like numerals are used to denote like components.

The fluid dispenser 10 shown in FIGS. 9 to 11 is identical to the fluid dispensers 10 shown in FIGS. 1 to 8, with the notable exception that the LEDs 44 are incorporated into the piston pump 16 rather than the pump mounting body 20.

As can be seen in FIG. 11, the upper terminal wall 54 of the piston chamber forming body 30 has a plurality of LEDs 44 that are arranged radially around a central axis of the pump 16. The LEDs 44 are configured to emit UV radiation downwardly into the air chamber 56 to sterilize the air chamber 56.

As can be seen in FIG. 10, the piston chamber forming body 30 has male electrical connectors 74 that extend rearwardly from the lock-out structure 38. The lock-out mechanism 32 of the pump mounting body 20 has corresponding female electrical connectors 76 that receive the male electrical connectors 74 when the piston pump 16 is received by the pump mounting body 20. The male electrical connectors 74 are connected to the LEDs 44 and connect the LEDs 44 to a power source via the female electrical connectors 76 when the piston pump 16 is received by the pump mounting body 20.

The inventors have appreciated that providing the LEDs 44 as part of the piston pump 16 has the advantage that, if the LEDs 44 fail, they can be replaced relatively quickly and easily merely by replacing the piston pump 16, without requiring maintenance or repairs to the housing 12.

Experimental Results

The inventors tested a variety of materials to assess their transparency to UV light with wavelengths in the range of about 200 nm to about 280 nm (UVC). The experiment used a split-beam spectrometer. Polycarbonate, Poly(methyl methacrylate) (PMMA), and Tritan™ Copolyester TX1001 were found to have poor transparency to UVC. Braskem™ RP350 was found to have some transparency to UVC; TOPAS™ 80075-04 COC was found to have good transparency to UVC; and quartz glass was found to have excellent transparency to UVC.

The inventors then tested whether UV light transmitted through different materials is effective at killing bacteria. Several petri dishes were inoculated with *E. coli* and *Pseudomonas aeruginosa*. The petri dishes were then covered with the materials to be tested (TOPAS™ 80075-04 COC and Braskem™ RP350), and exposed to UV light for either 15 seconds or 1 minute. Controls in which the petri dishes were covered by a UV blocking cover (control 1) or were left open with no cover (control 2) were also exposed to UV light for either 15 seconds or 1 minute. The petri dishes were then placed at 37 degrees Celsius to allow the bacteria to grow. The amount of bacteria growing on each petri dish was then measured, to calculate the logarithmic reduction factor for the different test materials and exposure times.

Figure 12:
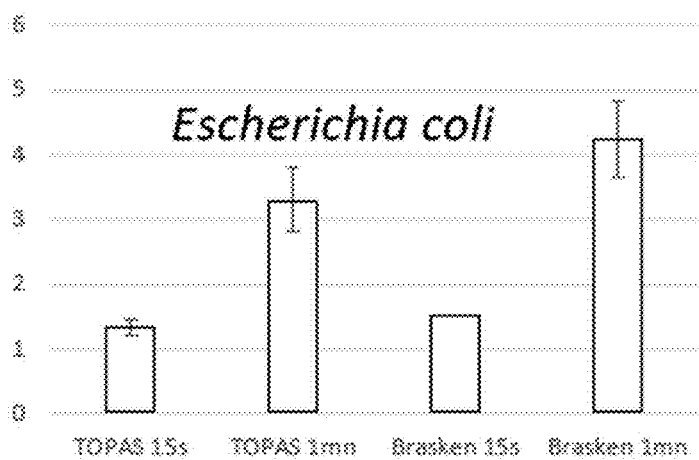
FIG. 12 is a bar graph showing the results of an experiment measuring the reduction factor of *E. coli* growth using different petri dish cover materials and UV exposure times.
Figure 13:
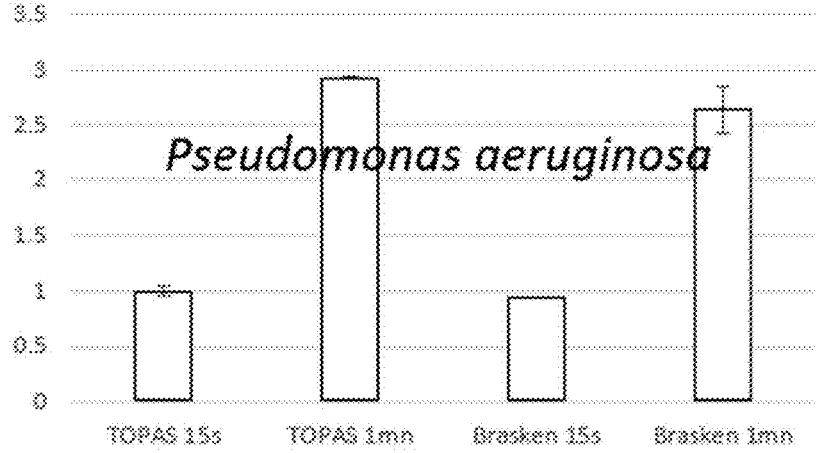
FIG. 13 is a bar graph showing the results of an experiment measuring the reduction factor of *P. aeruginosa* growth using different petri dish cover materials and UV exposure times.

The results of the experiment are shown in FIGS. 12 and 13. As can be seen in FIGS. 12 and 13, the UV light was effective at killing both *E. coli* and *Pseudomonas aeruginosa* through both TOPAS™ 80075-04 COC and Braskem™ RP350. The UV light was particularly effective at killing bacteria at the longer exposure time of 1 minute.

It will be understood that, although various features of the invention have been described with respect to one or another of the embodiments of the invention, the various features and embodiments of the invention may be combined or used in conjunction with other features and embodiments of the invention as described and illustrated herein.

The invention is not limited to the particular constructions of the fluid dispenser 10 shown in the preferred embodiments. Rather, any suitable construction for generating foam, and delivering a sanitizing wave such as UVC to the air chamber 56, could be used. For example, the fluid dispenser 10 could incorporate one or more of the features disclosed in U.S. Pat. No. 7,748,573 to Anhuf et al., issued Jul. 6, 2010; U.S. Pat. No. 5,975,360 to Ophardt, issued Nov. 2, 1999; U.S. Pat. No. 7,984,825 to Ophardt et al., issued Jul. 26, 2011; U.S. Pat. No. 8,397,949 to Ophardt, issued Mar. 19, 2013; U.S. Pat. No. 9,027,788 to Ophardt et al., issued May 12, 2015; U.S. Pat. No. 8,622,243 to Ophardt et al., issued Jan. 7, 2014; U.S. Pat. No. 8,733,596 to Ophardt et al., issued May 27, 2004; U.S. Pat. No. 7,455,197 to Ophardt, issued Nov. 25, 2008; U.S. Pat. No. 8,245,877 to Ophardt, issued Aug. 21, 2012; U.S. Pat. No. 8,113,388 to Ophardt et al., issued Feb. 14, 2012; U.S. Pat. No. 8,091,739 to Ophardt et al., issued Jan. 10, 2012; U.S. Pat. No. 8,684,236 to Ophardt, issued Apr. 1, 2014; U.S. Pat. No. 5,373,970 to Ophardt, issued Dec. 20, 1994; U.S. Pat. No. 5,836,482 to Ophardt et al., issued Nov. 17, 1998; U.S. Pat. No. 9,682,390 to Ophardt et al., issued Jun. 20, 2017; U.S. Pat. No. 10,242,301 to Ophardt et al., issued Mar. 26, 2019; U.S. Pat. No. 8,413,852 to Ophardt et al., issued Apr. 9, 2013; U.S. Pat. No. 8,113,388 to Ophardt et al., issued Feb. 14, 2012; and U.S. Pat. No. 7,455,197 to Ophardt, issued Nov. 25, 2008, which are incorporated herein by reference.

Although the invention has been described as preferably using UVC to sterilize the air chamber 56, any suitable type of electromagnetic radiation could be used instead. Furthermore, the invention is not limited to the use of LEDs 44, but could use any device capable of emitting suitable electromagnetic radiation. The invention could also use other types of waves for sanitizing the air chamber 56, such as ultrasonic waves. Both transverse and longitudinal types of waves could be used.

The air chamber 56 is also referred to herein as the air compartment 56. The liquid chamber 58 is also referred to herein as the liquid compartment 56. The air chamber 56 and the air piston element 66 together function as an air pump. The liquid chamber 58 and the liquid piston element 64 together function as a liquid pump. The ultraviolet light emitting diodes 44 are also referred to herein as the electromagnetic radiation emitter 44 and the wave emitter 44. The outer cylindrical wall 50 is also referred to herein as the compartment defining wall 50. The piston pump 16 is also referred to herein as the foam pump 16. The inner cylindrical wall 52 is also referred to herein as the internal wall 52. The trigger member 40 is also referred to herein as a switch 40. The closed upper end of the air compartment 56 is referred to herein as the first axial end, and the open bottom end of the air compartment 56 is referred to herein as the second axial end.

Preferably, the electromagnetic radiation emitter 44 is configured to emit electromagnetic radiation that is selected so as to avoid the generation of ozone within the air chamber 56.

Although this disclosure has described and illustrated certain preferred embodiments of the invention, it is to be understood that the invention is not restricted to these particular embodiments. Rather, the invention includes all embodiments which are functional, electrical, electromagnetic, optical, or mechanical equivalents of the specific embodiments and features that have been described and illustrated herein.

We claim:

1. A hand cleaning foam dispenser comprising:
a reservoir providing a supply of foamable liquid;
an air compartment providing a supply of air;
a foam generator that mixes the foamable liquid and the air to produce a foam;
a liquid pump for delivering the foamable liquid to the foam generator;
an air pump for delivering the air to the foam generator; and
a wave emitter that emits a wave into the air compartment to sanitize the air compartment;
wherein the wave emitter comprises an electromagnetic radiation emitter that emits electromagnetic radiation into the air compartment to sanitize the air compartment;
wherein the air compartment comprises a compartment defining wall;
wherein the electromagnetic radiation emitter is positioned outside of the air compartment;
wherein at least a portion of the compartment defining wall is formed from a material that permits the electromagnetic radiation to pass through the compartment defining wall into the air compartment;
wherein the hand cleaning foam dispenser further comprises a housing and a foam pump, the foam pump comprising the air compartment, the liquid pump, the air pump, and the foam generator;
wherein the housing is configured to removably receive the foam pump;
wherein the electromagnetic radiation emitter is arranged on the housing for emitting the electromagnetic radiation through the compartment defining wall into the air compartment when the foam pump is received by the housing;
wherein the electromagnetic radiation emitter is configured to only emit the electromagnetic radiation when the foam pump is received by the housing;
wherein the hand cleaning foam dispenser further comprises a switch that is activated when the foam pump is received by the housing;
wherein the electromagnetic radiation emitter is configured to only emit the electromagnetic radiation when the switch is activated;

wherein the housing has a lock-out mechanism to prevent unauthorized pumps from being received by the housing;
wherein the foam pump has a lock-out structure that engages with the lock-out mechanism when the foam pump is received by the housing; and
wherein the switch is located on or adjacent to the lock-out mechanism, so that the lock-out structure activates the switch when the foam pump is received by the housing.

2. The hand cleaning foam dispenser according to claim 1, wherein the electromagnetic radiation emitter emits ultraviolet radiation.

3. The hand cleaning foam dispenser according to claim 1, wherein the electromagnetic radiation emitter emits UVC with a wavelength of about 254 nm.

4. The hand cleaning foam dispenser according to claim 1, wherein the electromagnetic radiation emitter comprises an ultraviolet light-emitting diode (LED); and
wherein the ultraviolet LED uses less than 5 J of energy per second.

5. The hand cleaning foam dispenser according to claim 1, wherein the compartment defining wall is formed entirely from the material.

6. The hand cleaning foam dispenser according to claim 1, wherein the compartment defining wall has a window that is formed from the material.

7. The hand cleaning foam dispenser according to claim 1, wherein the material comprises at least one of: a cyclic olefin copolymer and a polypropylene random copolymer.

8. The hand cleaning foam dispenser according to claim 1, wherein the compartment defining wall is generally cylindrical, and the electromagnetic radiation emitter comprises a plurality of light-emitting diodes that are arranged radially around the compartment defining wall.

9. The hand cleaning foam dispenser according to claim 1, wherein the air compartment comprises a surface that absorbs the electromagnetic radiation.

10. The hand cleaning foam dispenser according to claim 9, wherein the surface comprises a material that has an antibacterial effect that is activated or enhanced when the surface is exposed to the electromagnetic radiation.

11. The hand cleaning foam dispenser according to claim 9, wherein the surface comprises a UV activated material;
wherein the UV activated material comprises titanium dioxide; and
wherein the UV activated material promotes photocatalytic production of reactive oxygen species when exposed to the electromagnetic radiation.

12. The hand cleaning foam dispenser according to claim 10, further comprising a liquid compartment that receives the foamable liquid from the reservoir;
wherein the air compartment has an internal wall, and the surface comprises an outer surface of the internal wall;
wherein the internal wall is cylindrical; and
wherein the outer surface surrounds the liquid compartment.

* * * * *